United States Patent [19]

Kim

[11] 4,152,356

[45] May 1, 1979

[54] METHOD FOR THE PREPARATION OF DIBENZOCYCLOHEPTENES FROM ANTHRACENE DERIVATIVES

[75] Inventor: Chang J. Kim, Somerset, N.J.

[73] Assignee: Exxon Research & Engineering Co., Florham Park, N.J.

[21] Appl. No.: 899,333

[22] Filed: Apr. 24, 1978

Related U.S. Application Data

[63] Continuation-in-part of Ser. No. 764,759, Feb. 2, 1977, abandoned.

[51] Int. Cl.$^2$ .......................... C07C 45/00; C07C 3/00
[52] U.S. Cl. .............................. 260/599; 260/600 R; 260/649 R; 568/808; 568/632; 568/633; 568/634; 585/320; 585/404
[58] Field of Search ............... 260/599, 600 R, 612 R, 260/613 R, 668 F, 649 R; 568/808

[56] References Cited

U.S. PATENT DOCUMENTS

3,409,640  11/1968  Schering ........................... 260/370.8

OTHER PUBLICATIONS

Tardieu, Chemical Abstracts, vol. 5 (1962) 5857–5860.
Noller, Textbook of Organic Chemistry, 2nd Ed. (1958). 134–135 & 154–155.
Bergmann et al., Tetrahedron Supplementary No. 8, Pt. 1 (1966) 141–148.
Flynn et al., Arkiv for Kemi, Band 27 nr. 32 (1967) 393–403.

Primary Examiner—Bernard Helfin
Attorney, Agent, or Firm—Ernest A. Forzano; David W. Collins

[57] ABSTRACT

This invention relates to a method of producing a dibenzocycloheptene compound of the structure

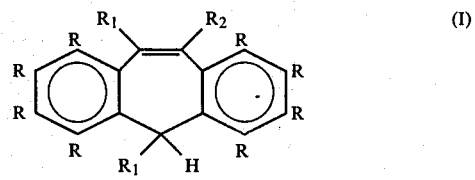

in high yields which comprises: (a) hydrogenating an anthracene derivative in the 9,10 position to form a 9,10-dihydroanthracene derivative, (b) selectively mono-carbonylating one of the hydrogens in the 9,10 position to form a monoaldehyde, (c) reducing the aldehyde to form the corresponding alcohol and (d) dehydrating and expanding the center ring to form the dibenzocycloheptene compound.

14 Claims, No Drawings

METHOD FOR THE PREPARATION OF DIBENZOCYCLOHEPTENES FROM ANTHRACENE DERIVATIVES

CROSS REFERENCE TO RELATED APPLICATION

This is a continuation-in-part application of Ser. No. 764,759, filed Feb. 2, 1977 and now abandoned.

BACKGROUND OF THE INVENTION

1. Field of the Invention

The invention relates to the preparation of dibenzocycloheptene and its derivatives.

2. Description of the Prior Art

The class of compounds having the structure

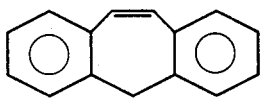

(A)

possesses valuable physiological characteristics. Among these are antidepressant, analgesic, and anticonvulsive properties.

Compound A and its derivatives are presently prepared via multistep, multistage synthesis which involves ring closure of double-ring compounds. U.S. Pat. No. 3,409,640 presents such a method. The final stage of this process involves the ring closure of double-ring structures, for example,

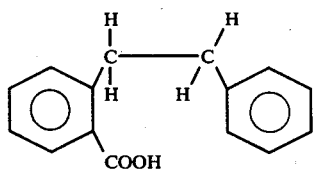

(2-phenylethylbenzoic acid). Such compounds are often expensive and/or not readily available. Therefore, it is necessary to prepare the double-ring compounds suitable for the above ring closure step. This additional preparation is time consuming and complex. In fact, as many as five steps may be added to the process because of the preparation of these double-ring compounds. (cf U.S. Pat. No. 3,409,640, col. 6, 1. 38, through col. 8, 1. 30).

The process presented by U.S. Pat. No. 3,409,640 is typical of the processes currently known to produce compound A and its derivatives in that such processes often involve reactants and compounds that are expensive or not readily available and/or involve numerous or complex preparative steps.

Compound A and its derivatives may also be prepared from anthracene and its derivatives as disclosed in Annales de Chimie (Paris) 6, 1445–1502 (1961) by dehydration of, e.g., 9,10-bis(hydroxymethyl)-9,10-dihydroanthracene. The alcohol is prepared by reduction with LiAlH$_4$ of the methyl ester of 9,10-dihydroanthracene-9-carboxylic acid, which in turn is separated and purified in less than 30% yield from a mixture containing other acids, e.g., 9,10-dihydroanthracene-9,10-dicarboxylic acid. The mixture of acids is the product of CO$_2$ reaction with sodium anthracide. Again, numerous preparative steps are required, and low yields of product are obtained.

SUMMARY OF THE INVENTION

The instant invention relates to a method of producing a dibenzocycloheptene compound of the structure

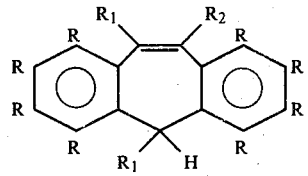

(I)

in high yields from an anthracene compound of the structure

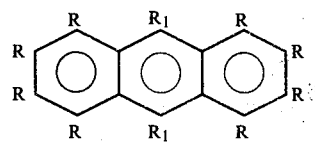

(II)

which comprises the steps described in detail below. R may be the same or different and is selected from the group consisting of hydrogen, C$_1$–C$_{10}$ straight chain alkyl, C$_3$–C$_{10}$ branched chain alkyl, C$_5$–C$_8$ cycloalkyl, halogen, C$_1$–C$_{10}$ straight chain alkoxy, C$_3$–C$_{10}$ branched chain alkoxy, and aromatic, wherein adjacent R groups may be members of cycloalkyl and aromatic rings fused to said compound II, wherein R$_1$ may be the same or different and is selected from R, provided R$_1$ is not a halogen, a straight or branched chain alkoxy, or members of cycloalkyl and aromatic structures fused to said compound II, and wherein R$_2$ is selected from hydrogen and alkyl and aromatic as defined for R.

The above process comprises the following steps (a) hydrogenating compound II to obtain a 9,10-dihydro compound of the structure

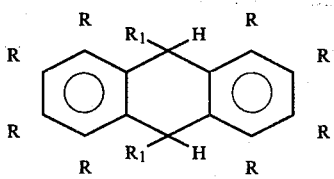

(III);

(b) highly selectively mono-carbonylating compound III according to the reaction

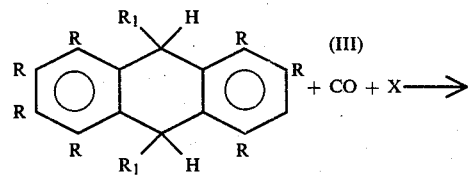

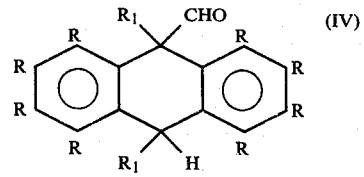

wherein X is a basic reactant capable of extracting one hydrogen atom from the 9,10-position, said basic reactant selected from the group consisting of metal alkoxide compounds, metal alkyl compounds, metal amide compounds and metal hydride compounds; (c) reducing compound IV to obtain a compound of the structure

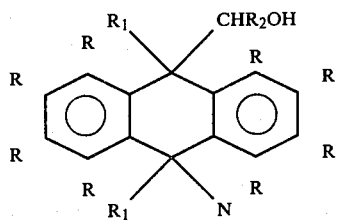 (V)

and isolating said compound V subsequent to said reduction; and (d) dehydrating and expanding the center ring of said isolated compound V to obtain compound I,

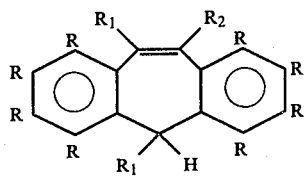 (I)

The selectivity of the above process in producing compound I ranges from about 40 to about 100 mole percent of the limiting reagent of this process, compound II. The yield of the above process in producing compound I ranges from about 40 to about 100 mole percent of the limiting reagent of this process, compound II.

The mono-carbonylation step, step (b), comprises reacting with carbon monoxide a reaction mixture of compound III and the basic reactant X combined in a formamide solvent. This reaction step is carried out at a temperature above the freezing point of the reaction mixture of step (b) up to and including 150° C., with the subsequent addition of a proton source to said reaction mixture to quench said reaction and product compound IV.

Unlike the processes of the prior art, the process of the instant invention presents a simple and economical method for the preparation of compound A,

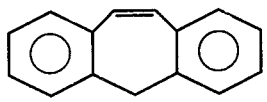

as well as for its derivatives enumerated below. The process of the instant invention utilizes relatively inexpensive compounds as starting materials. Anthracene,

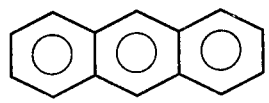

as well as the anthracene derivatives described in greater detail below, are the starting materials of the instant invention. In addition, the instant process is conducted under relatively mild conditions.

DETAILED DESCRIPTION OF THE INVENTION

This invention relates to a method of producing a compound of the structure

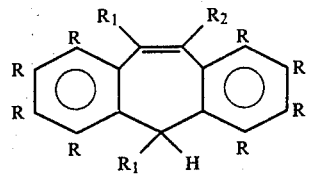 (I)

in high yields which comprises the steps of:
(a) hydrogenating a compound of the structure

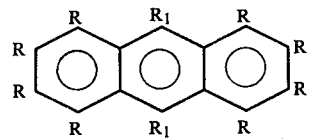 (II)

to obtain a compound of the structure

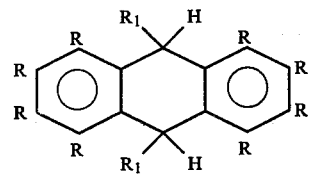 (III)

wherein R may be the same or different and is selected from the group consisting of hydrogen, $C_1$–$C_{10}$ straight chain alkyl, preferably $C_1$–$C_4$ straight chain alkyl, $C_3$–$C_{10}$ branched chain alkyl, preferably $C_3$–$C_4$ branched chain alkyl, $C_5$–$C_8$ cycloalkyl, halogen, $C_1$–$C_{10}$ straight chain alkoxy, preferably $C_1$–$C_4$ straight chain alkoxy, $C_3$–$C_{10}$ branched chain alkoxy, preferably $C_3$–$C_4$ branched chain alkoxy, and aromatic, wherein adjacent R groups may be members of cycloalkyl and aromatic rings fused to said compound II; however, R is preferably hydrogen, wherein $R_1$ may be the same or different and is selected from R, provided $R_1$ is not a halogen, a straight or branched chain alkoxy, or members of cycloalkyl and aromatic structures fused to said compound II;

(b) highly selectively mono-carbonylating said compound III to obtain a compound of the structure

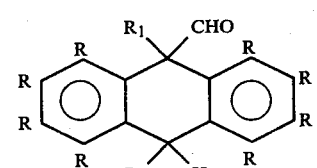 (IV)

according to the reaction

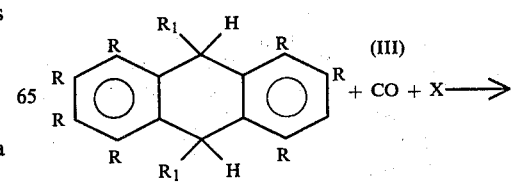

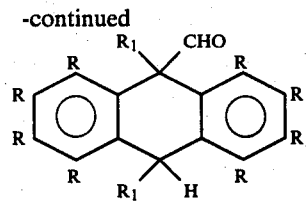 (IV)

wherein X is a basic reactant capable of extracting a hydrogen atom from the 9,10 position and is selected from the group consisting of metal alkoxide compounds, metal alkyl compounds, metal amide compounds and metal hydride compounds, preferably alkali metal alkoxide compounds, alkali metal alkyl compounds, alkali metal amide compounds and alkali metal hydride compounds, and wherein said monocarbonylating comprises reacting with carbon monoxide a reaction mixture which comprises said compound III and said basic reactant combined with a formamide solvent, said reaction occurring at a temperature above the freezing point of the reaction mixture of said step up to 150° C., with the subsequent addition of a proton source to said reaction mixture to quench said reaction and produce compound IV;

(c) reducing said compound IV to obtain a compount of the structure

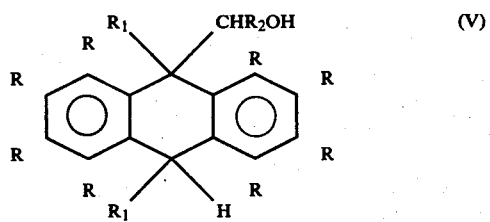 (V)

wherein $R_2$ is selected from hydrogen, alkyl as defined for R and aromatic as defined for R, preferably hydrogen, and isolating said compound V subsequent to said reduction; and (d) dehydrating and expanding the center ring of said isolated compound V to obtain said compound I

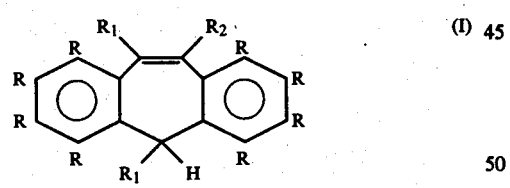 (I)

wherein the selectivity of said steps in producing said compound I ranges from about 40 to 100 mole percent of the limiting reagent of said process, compound II.

It has been unexpectedly discovered that the multi-step process of the instant invention produces compounds of the structure

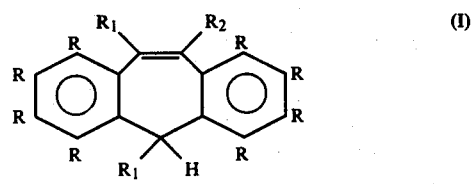 (I)

as defined above, from anthracene or certain of its derivatives in high yields with great selectivity.

Step (a) of this process can be summarized by the following reaction:

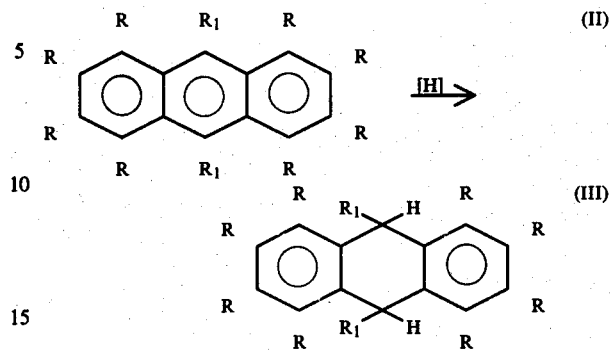

where R, $R_1$ and $R_2$ are as defined above. Details of the 9,10-dihydrogenation reaction of step (a) are readily available in the prior art and do not form a necessary part of this invention. For example, compound II may be hydrogenated to obtain compound III by conducting a reaction with alkali metals, e.g., Li, Na, K, Rb, Cs and hydrogen donors such as alcohols, amines and molecular hydrogen. This type of reaction, i.e., with the alkali metals and hydrogen donors, can be conducted utilizing a variety of solvents which include ethers, hydrocarbons, alcohols and amines. Those skilled in the art can select other methods to hydrogenate compound II to obtain compound III. The preferred method of hydrogenation is the alkali metal/hydrogen donor reaction described above. The selectivity of this step in the production of compound III ranges from about 80 to about 100 mole percent of compound II.

Step (b) of this process, the mono-carbonylation step, is a novel process in itself and is summarized by the following reaction:

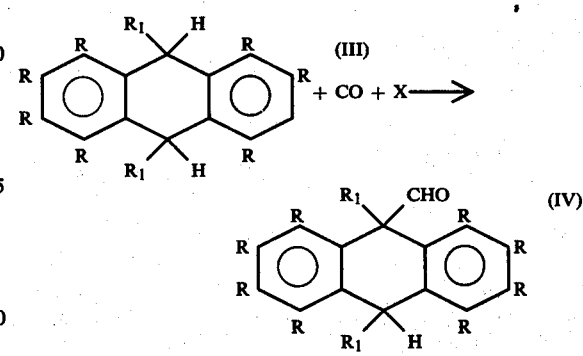

wherein X is a basic reactant capable of extracting one hydrogen atom from the 9,10 position. The remaining hydrogen in the 9,10 position (assuming the $R_1$ attached to the same carbon is a substituent other than hydrogen) occupies a cis- or trans- position in relation to the —CHO group.

There are two critical parameters of step (b), the basic reactant X and the solvent utilized in this step. As noted above, one of the requirements for this basic reactant is that it must be capable of extracting a hydrogen from one site selected from the 9- or 10- position of compound III. One class of compounds that will fulfill the requirements of this reactant in step (b) is a metal alkoxide compound. Examples include alkali metal alkoxide compounds, e.g., sodium methoxide, sodium 2-methoxyethoxide, potassium methoxide, potassium tertbutoxide, etc. Another class of compound that may be utilized in step (b) as a strong base is a metal alkyl compound, for example, alkali metal alkyl compounds, e.g., butyllithium (BuLi) and methyllithium (MeLi). Another compound fitting the requirements of a strong base in the reaction of step (b) is a metal amide compound, for example, alkali metal amide compounds, e.g., sodium amide, $NaNH_2$; potassium amide, $KNH_2$; lithium amide, $LiNH_2$; etc. Still another compound fitting the strong base requirements of step (b) is a metal hydride compound, e.g., alkali metal hydrides such as KH, NaH, LiH. Those skilled in the art will be able to select other strong bases compatible with the requirements of step (b).

As noted above, the solvent is another critical parameter of step (b). The classes of solvents represented by ethers, hydrocarbons, esters and sulfoxides were found to be unsatisfactory as solvents for the reaction in step (b). The preferred solvent for step (b) was found to be those compounds included within the class of formamide compounds, for example, dimethylformamide, N-formylpiperidene, and methylphenylformamide.

Since the reaction in step (b) requires a solvent from the class of formamide compounds, one need only add this type of solvent to the spent reaction mixture of step (a) to conduct the reaction of step (b). Hence, there would be no need to isolate products, decant off materials, etc. However, such isolation and separation steps may be taken, if desired. One particularly convenient embodiment would utilize an alkali metal and an amine solvent in step (a). Upon adding carbon monoxide for step (b), the amine solvent would be converted to a formamide in situ. Thus, in the above-enumerated embodiment there would be no need to add a formamide as such to the reaction vessel in order to conduct the reaction step (b) following step (a).

The quantity of each reactant required for step (b) parallels the stoichiometric amounts indicated in the chemical equation summarizing step (b) - one mole of strong base and one mole of carbon monoxide are needed for the carbonylation of one mole of compound III. However, as in most chemical reactions, it is advisable to start with a bit more than stoichiometric amounts to speed up the reaction.

The reaction in step (b) will proceed upon the mixing of the reactants in the desired solvent under the following operating conditions: temperature may be any temperature above the freezing temperature of the reaction mixture of step (b) up to about 150° C., preferably from about 0° C. to about 80° C.; pressure, from about 0.1 atm to 100 atm, preferably from about 1 atm to 50 atm. Compound III and the strong base need only be combined in a reaction vessel with the desired solvent to promote the reaction. Carbon monoxide can be introduced into the reaction of step (b) by a number of techniques. The techniques very familiar to those in the art include (1) the exertion of a carbon monoxide-rich atmosphere upon the liquid mixture containing the other reactants, or (2) directly bubbling carbon monoxide into the liquid reactant mixture. As noted above, there are other such techniques familiar to those in the art.

The reactants, compound III, CO and the strong base, do not technically produce compounds having the structure of compound IV

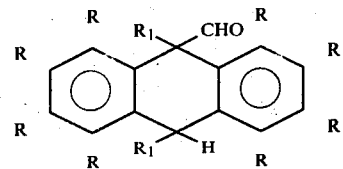

Rather, these reactants produce an anionic intermediate compound. Where $R_1$ in the 9-position is hydrogen, an example of such an anionic intermediate compound is

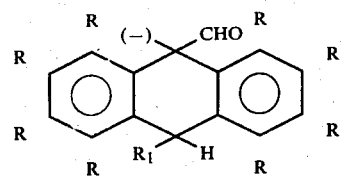

Again it is stressed that this is only one example of the possible intermediate compounds. To obtain a compound having the structure of compound IV, a proton source is introduced into the reaction mixture to quench it, thereby resulting in the formation of compound IV. For convenience, $H_2O$ is used. However, as in other base catalyzed reactions, acids (organic or mineral) may also be employed as proton sources, so long as the acid is employed in amounts that will not destroy the reducing agent, e.g., $NaBH_4$, employed in the next step of the process. Again, it must be emphasized that the introduction of $H_2O$ or other proton source will quench the reaction step (b) and, therefore, should not be introduced into the reaction until after the carbonylation reaction of step (b) is completed.

The reaction of step (b) produces mono-carbonylated species, compound IV, which is carbonylated at the 9- or 10-position, with great selectivity, between about 80 to 100 mole percent of compound III, the limiting reagent in step (b). In fact, even under extreme reaction conditions, for example, if a large excess of basic reactant is added or if a very high pressure of carbon monoxide is exerted upon the reaction mixture, the reaction of step (b) nevertheless stops at the mono-carbonylation stage.

The reduction of step (c) can be summarized by the following reaction:

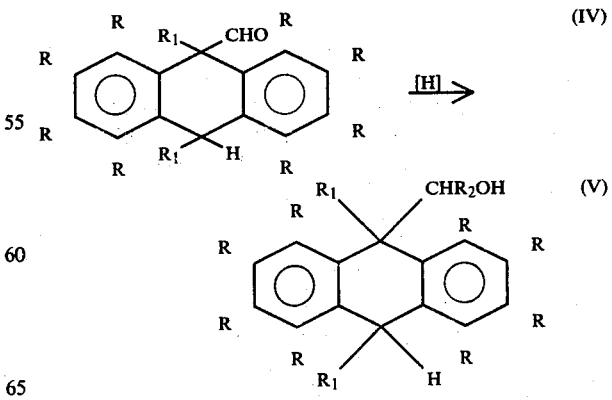

The 9,10-hydrogen (other than $R_1$) occupies a cis- or trans-position in relation to the $CHR_2OH$.

Various methods of reducing compound IV to compound V can be selected by those skilled in the art. Details of aldehyde reductions to alcohols are readily available in the prior art and do not form a necessary part of this invention, see, e.g., C. R. Noller, *Textbook of Organic Chemistry*, 2nd Ed., W. B. Saunders Co., Philadelphia (1958), pp. 154–155. As known by those skilled in the art, the isolation of compound IV may or may not be necessary prior to this reduction step depending upon the reduction method employed. For example, this isolation is necessary when the method of reduction employs a metal hydride, such as lithium aluminum hydride, or diborane, under anhydrous conditions. On the other hand, a reduction using sodium borohydride as the reducing agent does not require the isolation of compound IV prior to the reduction step. The preferred embodiment of the reaction of step (c) comprises the treating of the reaction mixture of step (b) with an aqueous solution of sodium borohydride or its analogs. Utilizing this embodiment, the yield of compound V is essentially 100 mole % of compound IV, the limiting reagent of step (c). Alternative methods of reduction can be selected by those skilled in the art. In the resulting product from such aldehyde reductions, $R_2$ is hydrogen. Such reductions are preferred.

Instead of directly reducing the aldehyde group, —CHO, added to compound IV in step (b), one may perform Grignard and related reactions to obtain a variety of secondary alcohols (—CHR$_2$OH) at the site of this —CHO group, see, e.g., the Noller reference cited above. Here, $R_2$ is selected from the group consisting of $C_1$-$C_{10}$ straight chain alkyl, preferably $C_1$-$C_4$ straight chain alkyl, $C_3$-$C_{10}$ branched chain alkyl, preferably $C_3$-$C_4$ branched chain alkyl, $C_5$-$C_8$ cycloalkyl and aromatic. The dehydration and expansion reaction of step (d) would in this case lead to a compound having the structure of compound I,

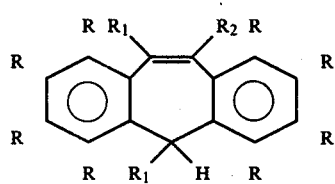

where $R_2$ is the alkyl or aromatic group substituted during the Grignard step. For example, beginning with compound IV having the structure

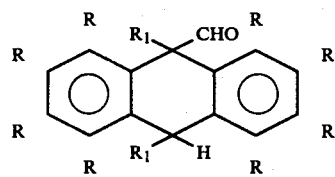

after the Grignard step a secondary alcohol would result at the site of the —CHO group. This compound would have the structure

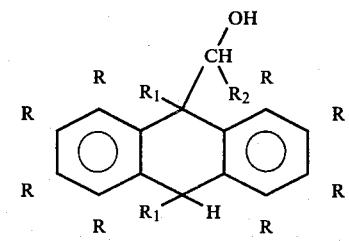

where $R_2$ is an alkyl or an aromatic group, preferably as defined above. After step (d), the dehydration and ring expansion step, the compound produced would have the structure of compound I, where either an alkyl or an aromatic group is at the 11 position.

The dehydration-rearrangement reaction of step (d) is summarized by the following chemical equation:

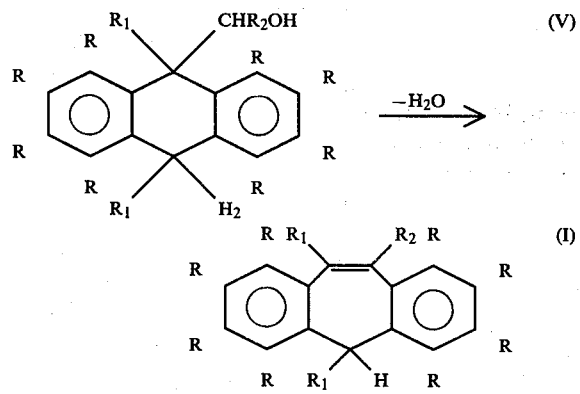

where R, $R_1$ and $R_2$ are as defined above.

Again, a variety of methods can be utilized to form compound I which include an acid catalyzed dehydration of V or solvolysis of the derivatives of V, e.g., sulfonate derivatives, carboxylate derivatives or halide derivatives. Details of the dehydration and ring expansion reaction are described elsewhere; see, e.g., Annales de Chimie (Paris) 6, 1445–1502 (1961); Arkiv for Kemi 27 (32), 393–403 (1967); and Tetrahedron Supplement, No. 8, Pt. 1, 141–148 (1966) and thus do not form a necessary part of this invention.

In the preferred embodiment of step (d), compound V is converted to compound I utilizing a variety of acid catalysts such as silica-alumina, zinc chloride and potassium hydrogen sulfate. Those skilled in the art will be able to select other acid catalysts as well as other processes to accomplish the dehydration-rearrangement of step (d).

The selectivity of step (d) in producing compound I can range from about 80 to 100 mole percent of compound V, the limiting reagent of step (d), when utilizing an acid catalyst to promote the dehydration and rearrangement step. Those skilled in the art can select the operating conditions for the particular route selected in step (d).

Before converting compound V to compound I, in step (d), it is necessary to first isolate compound V from step (c). This may be achieved by simple extraction or recrystallization, employing methods well-known in the art for isolating primary or secondary alcohols. This is the only step that requires isolation. Except as noted above, steps (a), (b) and (c) can be carried out in one batch without an intermediate isolation of products.

Conversely, the process can be stopped after any step to obtain high yields of compounds III, IV or V. Moreover, one may use this process starting step (b) with compound III, the hydrogenated product of anthracene, or its qualified derivative.

The overall selectivity of this multistep process in producing compound I ranges between about 40 to about 100 mole % of compound II, the limiting reagent of the entire process, when a variety of alternative methods in steps (a), (c) and (d) is utilized.

When the instant invention is used to prepare compounds having the structure of compound I

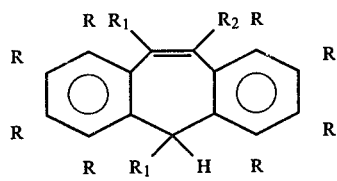

the 5-, 10- and 11- positions can be selectively activated by a variety of substitution, addition or oxidation reactions known in the art. By this procedure, a vast number of dibenzocycloheptane-derived drugs can be prepared.

While substitutents in the 9, 10 position have been schematically depicted herein as coplanar with the aromatic rings, it will be appreciated by those skilled in the art that in each of the reaction steps following the 9, 10-dihydrogenation reaction, cis- or trans- relationships involving —CHO (or —CHR$_2$OH) can exist where R$_1$ is a substituent other than hydrogen. Accordingly, it will be appreciated that the claims herein are not limited to any particular stereospecific route.

The following examples are submitted to illustrate and not to limit the invention.

EXAMPLE 1

A mixture of 3.5 grams anthracene, 1.1 grams sodium metal, 3.5 cc of 2-methoxyethanol and 20 cc of o-xylene was refluxed for three hours under a nitrogen atmosphere. The mixture was allowed to cool to room temperature. The mixture was then transferred to a 150 cc autoclave; and 25 cc of dimethylformamide (DMF) was added and was flushed with CO which was then used to pressurize the system to 600 psig, then stirred at ambient temperature for five hours and the residual CO was released. The autoclave was opened and a sodium borohydride solution (0.5 grams in 10 cc of water) was added to the mixture, followed by stirring at room temperature for one hour. Excess hydride was neutralized by adding a hydrochloric acid solution. The product was extracted with ether, washed with water, and the solvents were evaporated off. The final product mixture contained 80% of

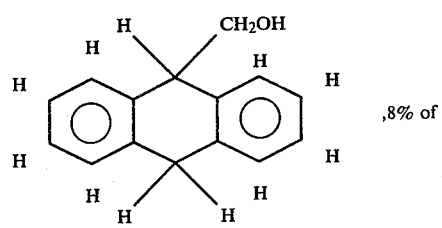

,8% of

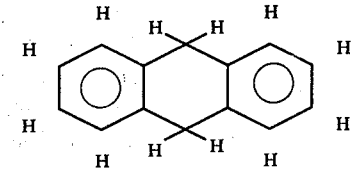

and 12% unreacted starting material, i.e.

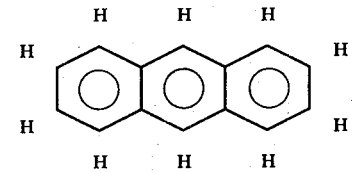

A one-step recrystallization from pentane-benzene gave 2.8 grams of

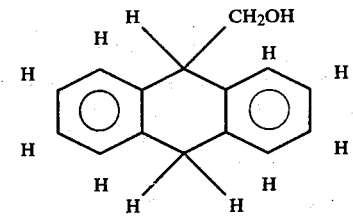

1.0 grams of this compound was heated with 2.0 grams of zinc chloride to 200° C. This mixture was taken up in a benzene-water mixture. The amount of pure

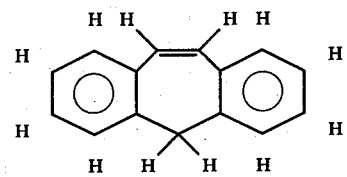

isolated from recrystallization from a methanol-benzene solution was 0.9 grams, melting point: 131° C.

EXAMPLE 2

An automatic gas reactor (Brown Square Apparatus, U.S. Pat. No. 3,180,710) was set up for carbon monoxide generation by charging the buret with formic acid and the generating flask with 96% sulfuric acid. To the reactor flask, which was under a nitrogen atmosphere, was added 3.6 grams of 9,10-dihydroanthracene, 4.0 grams of sodium methoxide, and 30 cc of DMF. To dissolve the hydrocarbon, the mixture was heated to about 80° C. with stirring, and then cooled to room temperature. The stirring was stopped, the nitrogen was flushed out with carbon monoxide, and vigorous stirring was commenced. Immediate carbon monoxide uptake was observed. After overnight stirring, water was added to the mixture, and then 30 cc of 10% hydrochloric acid solution was added slowly. The mixture was extracted twice with 50 cc portions of diethyl ether. The combined ether solution was washed with water and then with sodium bicarbonate solution. A gas chromatographic analysis showed the presence of 9,10-dihydro-9-anthraldehyde in a 73% yield together with 22% of the unreacted starting material.

EXAMPLE 3

A glass-lined 150 milliliter autoclave was charged with 3.6 grams of 9,10-dihydroanthracene, 1.0 grams of sodium methoxide and 25 cc of DMF. The autoclave was flushed with a CO-H$_2$ (1:1) mixture, which was then used to pressurize the system to 600 psig. Within a few minutes from the start of the stirring, the pressure dropped to 500 psig. The mixture was then heated briefly to 100° C. and allowed to cool to room temperature overnight. An analysis of the product revealed the formation of 9,10-dihydro-9-anthraldehyde in a 95% yield. No other products were detected.

EXAMPLE 4

According to the procedure described in Example 3, a mixture of 9.0 grams of 9,10-dihydroanthracene, 3.5 grams of sodium methoxide and 25 cc of DMF was treated with carbon monoxide under an initial pressure of 800 psig. At the end, residual CO (400 psig) was released, and a sodium borohydride solution (1 gram in 10 cc of water) was added to the mixture. Excess hydride was destroyed by adding a hydrochloric acid solution. The mixture was then extracted with ether. An 83% yield of 9,10-dihydro-9-anthracenemethanol was realized. The separation was carried out by evaporating off the solvent, then extracting the desired product from the residue with methanol. Recrystallization from benzene-pentane gave 6.0 grams of white powder, mp=105° C. which was identified as 9,10-dihydro-9-anthracenemethanol. Five grams of this product was mixed with 1.0 grams of silica-alumina (Davison SMR5-1020, 87% SiO$_2$-13% Al$_2$O$_3$, BET surface area 350 m$^2$/gr) and heated under a nitrogen flow to 250° C. After cooling, the solid was dissolved in benzene, and methanol was added to recrystallize 4.5 grams of white plates which was identified to be pure 5H-dibenzo(a,d)cycloheptene, i.e. a compound having the structure of compound I.

EXAMPLE 5

In a manner similar to Example 1, a mixture consisting of 9-methylanthracene (3.9 grams), i.e.

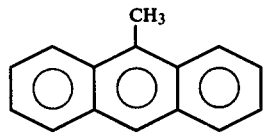

metallic sodium (1.0 grams), tert-butanol (5 cc) and toluene (25 cc) was charged in an autoclave and heated to 140° C. for two hours. After the mixture was cooled to room temperature, 25 cc of DMF was added, followed by pressurizing the autoclave with carbon monoxide to 400 psig. The temperature was raised to 140° C., and kept at this temperature for two hours with stirring. After overnight cooling, the excess pressure was released and 0.5 grams of sodium borohydride in 10 cc of water was added to the mixture. After utilizing the separation technique used in Example 4, the mixture was analyzed by both glpc and NMR to contain 27% of unreacted starting material, 10% of 9,10-dihydro-9-methylanthracene, and 55% of 9,10-dihydro-10-methyl-9-anthrylcarbinol, i.e.

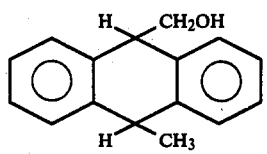

EXAMPLE 6

A 150 cc autoclave was charged with 3.5 grams of anthracene, 1.0 grams of sodium metal, 5 cc of tert-butanol, 15 cc of piperidine and 15 cc of toluene. The mixture was heated to 130° C. under a nitrogen atmosphere for 2 hours with constant stirring. The autoclave was then pressurized with CO to 300 psig. A rapid pressure drop was observed. When the pressure dropped below 200 psig, more CO was added. This operation was repeated until no further pressure drop was observed over the period of an hour. The vessel was then cooled, the excess pressure released, and the reaction mixture was treated with aqueous sodium borohydride as in the previous examples. After the excess hydride was destroyed, 50 cc of 10% hydrochloric acid was added, and the mixture was extracted three times with 50 cc portions of ether. The combined ether extract solutions were washed successively with 10% HCl solution, water and 10% Na$_2$CO$_3$ solution. Evaporation of the solvent left 4.1 grams of residue comprising 84.2% of 9,10-dihydro-9-anthracenemethanol, i.e.

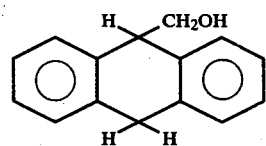

11.7% starting material, and 4.1% 9,10-dihydroanthracene, i.e.

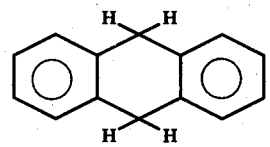

The 9,10-dihydro-9-anthracenemethanol was isolated as a white powder with a melting point of 104°-105° C. The aqueous wash solutions were saturated with salt and extracted twice with 50 cc portions of ether. These two extractions were combined and dried over sodium sulfate, filtered and the solvent was stripped off. Five grams of oil remained which was identified by NMR, IR and glpc to be N-formylpiperidene.

What is claimed is:

1. A method of producing a compound of the structure

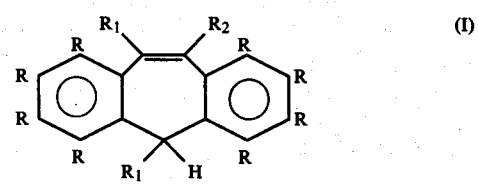

in high yields which comprises the following steps:

(a) hydrogenating a compound of the structure

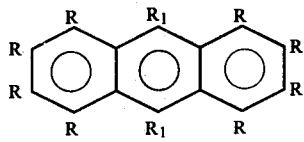

to obtain a 9,10-dihydrogenated compound of the structure

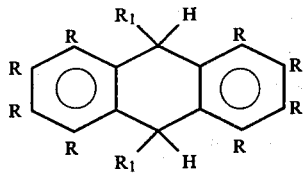

wherein R may be the same or different and is selected from the group consisting of hydrogen, $C_1$–$C_{10}$ straight chain alkyl, $C_3$–$C_{10}$ branched chain alkyl, $C_5$–$C_8$ cycloalkyl, halogen, $C_1$–$C_{10}$ straight chain alkoxy, $C_3$–$C_{10}$ branched chain alkoxy, and aromatic, wherein adjacent R groups may be members of cycloalkyl and aromatic rings fused to said compound II, and wherein $R_1$ may be the same or different and is selected from R, provided $R_1$ is not a halogen, a straight or branched chain alkoxy, nor members of cycloalkyl and aromatic structures fused to said compound II;

(b) highly selectively mono-carbonylating said compound III to obtain a compound of the structure

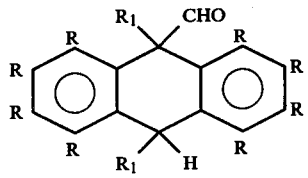

according to the reaction

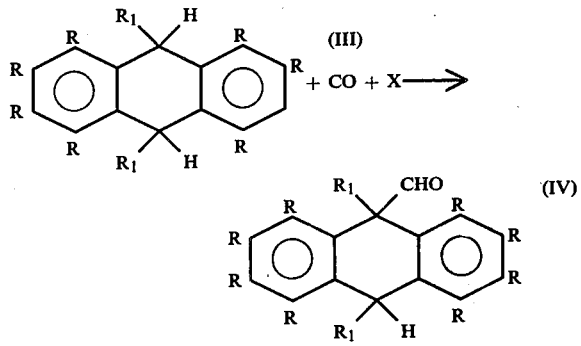

wherein X is a basic reactant capable of extracting one hydrogen atom from the 9,10 position and is selected from the group consisting of metal alkoxide compounds, metal alkyl compounds, metal amide compounds and metal hydride compounds, said mono-carbonylating comprises reacting with carbon monoxide a reaction mixture which comprises said compound III and said basic reactant combined with a formamide solvent, said reaction occurring at a temperature in the range of about 150° down to any temperature above the freezing point of said reaction mixture of step (b) with the subsequent addition of a proton source to said reaction mixture to quench said reaction and produce said compound IV;

(c) reducing said compound IV to obtain a compound of the structure

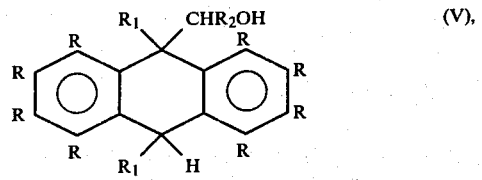

wherein $R_2$ is selected from the group consisting of hydrogen, alkyl as defined for R and aromatic as defined for R and isolating said compound V subsequent to said reduction; and (d) dehydrating and expanding the center ring of said isolated compound V to obtain said compound I,

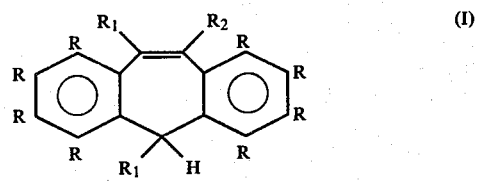

wherein the selectivity of said steps in producing said compound I ranges from about 40 to 100 mole percent of the limiting reagent of said process, said compound II.

2. The method of claim 1 wherein said formamide solvent in step (b) is selected from the group consisting of dimethylformamide, N-formylpiperidene, and methylphenylformamide.

3. The method of claim 1, wherein said formamide solvent in said step (b) is produced in situ by reacting said carbon monoxide reactant of said step (b) with the reactant mixture of said step (a), which contains an alkali metal and an amine solvent.

4. The method of claim 1 wherein X is selected from the group consisting of alkali metal alkoxide compounds, alkali metal alkyl compounds, alkali metal amide compounds and alkali metal hydride compounds.

5. The method of claim 1, wherein the selectivity of said mono-carbonylating step in the production of said compound IV ranges from about 80 to 100 mole percent of the limiting reagent of said mono-carbonylating step, said compound III.

6. The method of claim 1 wherein R may be the same or different and is selected from the group consisting of hydrogen, $C_1$–$C_4$ straight chain alkyl, $C_3$–$C_4$ branched chain alkyl, $C_5$–$C_8$ cycloalkyl, halogen, $C_1$–$C_4$ straight chain alkoxy, $C_3$–$C_4$ branched chain alkoxy and aromatic.

7. The method of claim 6 wherein R is hydrogen.

8. The method of claim 1 wherein $R_2$ is hydrogen.

9. The highly selective mono-carbonylation of a compound of the structure

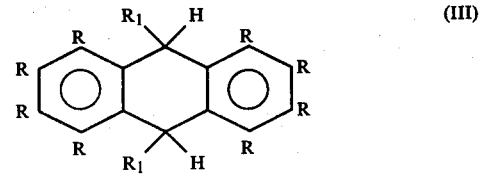

to obtain a compound of the stucture

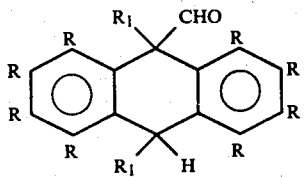

wherein R may be the same or different and is selected from the group consisting of hydrogen, $C_1$–$C_{10}$ straight chain alkyl, $C_3$–$C_{10}$ branched chain alkyl, $C_5$–$C_8$ cycloalkyl, halogen, $C_1$–$C_{10}$ straight chain alkoxy, $C_3$–$C_{10}$ branched chain alkoxy, and aromatic, wherein adjacent R groups may be members of cycloalkyl and aromatic rings fused to said compound III, and wherein $R_1$ may be the same or different and are selected from the group consisting of hydrogen, $C_1$–$C_{10}$ straight chain alkyl, $C_3$–$C_{10}$ branched chain alkyl, $C_5$ to $C_8$ cycloalkyl, and aromatic, and said monocarbonylating, proceeds according to the reaction:

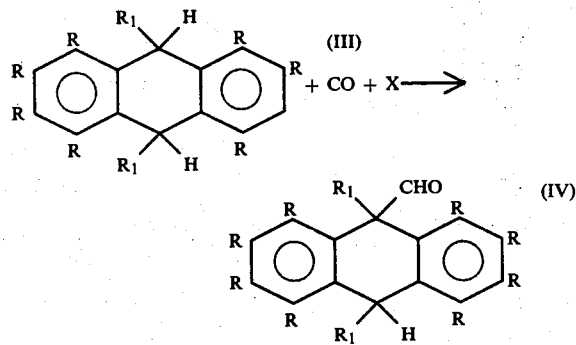

wherein X is a basic reactant capable of extracting one hydrogen from the 9,10 position and is selected from the group consisting of metal alkoxide compounds, metal alkyl compounds, metal amide compounds and metal hydride compounds, wherein said mono-carbonylation comprises reacting with carbon monoxide a reaction mixture which comprises said compound III and said basic reactant combined with a formamide solvent, said reaction occurring at a temperature in the range of about 150° C. down to any temperature above the freezing point of said reaction mixture of said mono-carbonylation, with the subsequent addition of a proton source to said reaction mixture to quench said reaction and produce said compound IV.

10. The method of claim 9 wherein X is selected from the group consisting of alkali metal alkoxide compounds, alkali metal alkyl compounds, alkali metal amine compounds and alkali metal hydride compounds.

11. The method of claim 9 wherein the selectivity of said mono-carbonylation in the production of said compound IV ranges from about 80 to 100 mol percent of the limiting reagent of said process, said compound III.

12. The method of claim 9 wherein said formamide solvent is selected from the group consisting of dimethylformamide, N-formylpiperidene, and methylphenylformamide.

13. The method of claim 9 wherein R may be the same or different and is selected from the group consisting of hydrogen, $C_1$–$C_4$ straight chain alkyl, $C_3$–$C_4$ branched chain alkyl, $C_5$–$C_8$ cycloalkyl, halogen, $C_1$–$C_4$ straight chain alkoxy, $C_3$–$C_4$ branched chain alkoxy and aromatic and wherein $R_1$ may be the same or different and is selected from the group consisting of hydrogen, $C_1$–$C_4$ straight chain alkyl, $C_3$–$C_4$ branched chain alkyl, $C_5$–$C_8$ cycloalkyl and aromatic.

14. The method of claim 13 wherein R is hydrogen.

* * * * *